US00PP26175P3

(12) United States Plant Patent
Bacon

(10) Patent No.: US PP26,175 P3
(45) Date of Patent: Dec. 1, 2015

(54) PLUM TREE NAMED 'SUPLUMFORTYFIVE'

(50) Latin Name: *Prunus salicina*
Varietal Denomination: Suplumfortyfive

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 85 days.

(21) Appl. No.: 13/998,414

(22) Filed: Oct. 30, 2013

(65) Prior Publication Data

US 2015/0121577 P1 Apr. 30, 2015

(51) Int. Cl.
*A01H 5/08* (2006.01)

(52) U.S. Cl.
USPC ..... Plt./184

(58) Field of Classification Search
USPC ..... Plt./184
See application file for complete search history.

*Primary Examiner* — Keith O. Robinson

(74) *Attorney, Agent, or Firm* — Knobbe, Martens, Olson & Bear, LLP

(57) ABSTRACT

A new and distinct plum tree variety, *Prunus salicina*, cv. 'Suplumfortyfive' is characterized by early ripening fruit that has dark greyed-purple skin and red flesh, is high in sugar, has low acidity, is very juicy and has mild flavor.

1 Drawing Sheet

Latin name of the genus and species claimed: *Prunus salicina.*

Variety denomination: 'Suplumfortyfive'.

BACKGROUND AND SUMMARY OF THE INVENTION

This invention relates to the discovery and asexual propagation of a new and distinct variety of plum, *Prunus salicina* cv. 'Suplumfortyfive'. The new variety was first originated by hybridization in June 2004 by Terry A. Bacon as breeder number: 'PL878RB'.

The new variety 'Suplumfortyfive' is characterized by early ripening, a dark greyed-purple skin with red flesh, and fruit that is high in sugar and has low acidity. The fruit of the new variety 'Suplumfortyfive' is also very juicy and has a mild flavor.

The seed parent is 'Suplumeleven' (U.S. Plant Pat. No. 4,902), and the pollen parent is unknown, being from a bulk of pollen from four plum varieties. The parent varieties were first crossed in March 2001, with the date of first sowing being January 2002, and the date of first flowering being March 2003. The new plum variety 'Suplumfortyfive' was first asexually propagated by Terry Bacon near Wasco, Kern County, Calif. in January 2002 by budding.

The new variety 'Suplumfortyfive' is distinguished from its seed parent in that the harvest of the new variety starts June 11 while the harvest of the seed parent Plum Tree named 'Suplumeleven' (U.S. Plant Pat. No. 4,902) starts July 1$^{st}$.

The new variety 'Suplumfortyfive' ripens at a similar time to 'Early Queen' (U.S. Plant Pat. No. 8,583) but the fruit of the new variety 'Suplumfortyfive' has a red flesh compared to the amber flesh of the fruit of 'Earliqueen' (U.S. Plant Pat. No. 8,583). The new variety 'Suplumfortyfive' ripens at the same time as 'Black Splendor' (unpatented) but the fruit of the new variety 'Suplumfortyfive' has a mild skin compared to the tart-bitter skin on 'Black Splendor' (unpatented) when firm-mature.

The new variety 'Suplumfortyfive' has been shown to maintain its distinguishing characteristics through successive asexual propagations by, for example, budding.

BRIEF DESCRIPTION OF THE PHOTOGRAPH

The accompanying color photographic illustration shows typical specimens of the foliage and fruit of the present new plum variety 'Suplumfortyfive'. The illustration shows the upper and lower surface of the leaves, a view of the fruit as a whole, and a sectional view of a fruit divided across its suture plane to show flesh color, pit cavity and the stone remaining in place in an 8 year old plant. The photographic illustration was taken shortly after being picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 8 year old 'Suplumfortyfive' plants, grown in the vicinity of Wasco, Kern County, Calif., during 2013, and is believed to apply to plants of the variety grown under similar conditions of soil and climate elsewhere.

TREE

General: (Measurements taken on an 8 year old tree unless otherwise noted.)

*Size.*—Medium.

*Spread.*—Approximately 3-5 meters.

*Vigor*.—Vigorous, about 2 m in height the first growing season.
*Growth*.—Semi-upright.
*Productivity*.—Productive.
*Form*.—Vase formed.
*Bearer*.—Regular.
*Fertility*.—Unknown.
*Canopy density*.—Medium.
*Hardiness*.—Hardy in all fruit growing areas of California. Winter chilling requirement is approximately 600 hours at or below 7.2 C.
*Disease resistance/susceptibility*.—Under close observation in Kern County, Calif., no particular plant/fruit disease resistance/susceptibility has been observed.
*Insect resistance/susceptibility*.—Under close observation in Kern County, Calif., no particular plant/fruit insect resistance/susceptibility has been observed.

Trunk: (Measurements at approximately 30 cm above soil line on mature tree).
*Length*.—Approximately 61 cm.
*Diameter*.—Approximately 20 cm, it varies with soil type, fertility, climatic conditions and cultural practices.
*Texture*.—Medium shaggy, increases with age of tree.
*Trunk color*.—About Medium Grey-Brown 199B to Dark Brown 200B; becomes darker with age.

Branches: (Measurements at approximately 90 cm above soil line.)
*Length*.—Approximately 240 cm.
*Size*.—Diameter approximately 9 cm.
*Texture*.—Smooth on first year wood, increasing in roughness with tree age.
*Color*.—Varying from about Medium Grey-Brown 198B to Dark Brown 200B.
*Lenticels*.—Present.

Lenticels:
*Density*.—Varies with tree vigor and climatic conditions, about 2/cm$^2$.
*Color*.—About Medium Grey-Brown 199B.
*Size*.—Medium, about 1 mm×2 mm.
*Length*.—3 mm.
*Width*.—2 mm.

Flowering shoots: (Data taken in July at mid-point of current season growth.)
*Size*.—Average diameter approximately 5 mm.
*Color*.—Topside: About Medium Green 139A to Medium Greyed-Purple 185B. Underside: About Medium Green 139A.
*Internode length*.—Medium; approximately 3 cm. Midway on flowering shoot.
*Flowering shoot lenticels*.—Moderate, about 8/cm$^2$. Color: About Medium Grey-Brown 199B. Diameter: Approximately 1 mm.
*Flowering shoot leaf buds*.—Shape: Obovate. Width: Approximately 1.5 mm. Length: Approximately 2.1 mm. Color: About Dark Greyed-Orange 177A. Texture: Smooth.
*Flowering shoot flower buds*.—Shape: Elliptic. Width: Approximately 1 mm. Length: Approximately 1.8 mm. Color: About Dark Greyed-Orange 177A. Number of buds per node: Usually 2. Texture: Smooth.
*Density of flower buds*.—Medium, about 2-4/node.
*Density of leaf buds*.—Medium, about 1-4/node.
*Flower bud distribution*.—On spurs and one year old shoots.
*Ratio of wood (leaf) buds to flowering buds*.—1/2 on nodes.
*Anthocyanin intensity*.—None or very slight.
*Spurs length*.—Medium, approximately 0.8 mm.
*Vegetative bud size*.—Medium, approximately 1.55 mm wide and 2.1 mm long.
*Position of vegetative bud in relation to shoot*.—Slightly held out.

FOLIAGE

Leaves: (Data taken in July on fully expanded leaves at mid-point of the current season growth).
*Size*.—Medium.
*Average length*.—Medium; approximately 75 mm.
*Average width*.—Medium; approximately 45 mm.
*Thickness*.—Medium, approximately 0.8 mm.
*Color*.—Upper surface: About Dark Green 135A. Lower surface: About Medium Green 135C.
*Form*.—Broad obovate.
*Tip*.—Cuspidate.
*Base*.—V-shaped.
*Margin*.—Crenate.
*Venation*.—Pinately net veined.
*Vein color*.—About Light Green 135D.
*Surface texture*.—Smooth (upper and lower).
*Leaf blade (ratio of length to width)*.—Slightly elongated.
*Shape in the cross section*.—Flat.
*Angle at apex*.—Small.
*Profile*.—Flat.
*Leaf blade tip*.—Slightly curved downward.
*Angle of tip*.—Acute.
*Undulation of margin*.—Slight.
*Glossiness of upper side*.—Medium.
*Density of pubescence of lower side*.—Sparse.
*Position of nectaries*.—Predominantly on petiole.

Petiole:
*Texture*.—Smooth.
*Strength*.—Strong.
*Average length*.—Medium; approximately 10 mm.
*Average diameter*.—Approximately 2 mm.
*Color*.—About Light Green 135D with red highlights, about Medium Greyed-Purple 185B, where there is more light exposure.

Stipules:
*Texture*.—Smooth (upper and lower surfaces).
*Number/leaf bud*.—Approximately 1 per leaf bud when present.
*Typical length*.—Approximately 3 mm.
*Color*.—About Medium Greyed-Orange 164B.
*Persistence*.—Falls off.

Leaf glands:
*Form*.—Globose.
*Average number*.—Usually 2.
*Position*.—On petiole, alternate.
*Average size*.—Medium; approximately 0.7 mm by 07.mm.
*Color*.—About Medium Grey-Brown 199B.

FLOWERS

General:
*Flower blooming period*.—First bloom: Approximately February 24 in Wasco, Calif. Full bloom: Approximately February 28 in Wasco, Calif.

*Location of first bloom*.—Older wood.
*Location of full bloom*.—Uniform throughout the canopy.
*Time of bloom*.—Medium from approximately February 24-February 28.
*Duration of bloom*.—Medium; approximately 12 days.
*Diameter of fully opened flower*.—Medium, approximately 10 mm.
*Flower aroma*.—Very slight.
*Shape*.—Rosaceous.

Peduncle:
*Strength*.—Strong.
*Length*.—Medium; approximately 10 mm.
*Diameter*.—Medium; approximately 1 mm.
*Color*.—About Medium Yellow-Green 144B.
*Pubescence*.—Absent.

Petals:
*Number*.—5.
*Arrangement*.—Overlapping slightly.
*Length*.—Approximately 12 mm.
*Diameter*.—Approximately 10 mm.
*Shape*.—Obovate.
*Apex shape*.—Rounded.
*Base shape*.—Narrows at point of attachment.
*Color of inner and outer surface*.—Approximately White 155D.
*Surface texture*.—Smooth.
*Margins*.—Slightly undulating.
*Frequency of flowers with double petals*.—None.
*Size*.—Medium, approximately 10 mm width.
*Claw length*.—Medium, approximately 1.5 mm.
*Margin waviness*.—Medium.
*Base angle*.—Narrow.
*Division of upper margin*.—Entire.
*Pubescence of inner surface*.—Absent.
*Pubescence of outer surface*.—Absent.

Sepals:
*Number*.—5.
*Length*.—Approximately 3 mm.
*Diameter*.—Approximately 2 mm.
*Shape*.—Triangular.
*Color*.—About Medium Yellow-Green 144A.
*Surface texture*.—Smooth (upper and lower).
*Margins*.—Entire.
*Positioning*.—Adpressed to petals.
*Pubescence of inner surface*.—Absent.
*Pubescence of outer surface*.—Absent.
*Frequency of flowers with double sepals*.—None.

Stamens:
*Number*.—Ranges from about 20 to 30, averages 25.
*Average length*.—About 7 mm.
*Filament color*.—Approximately White 155D.
*Anther color*.—About Medium Greyed-Orange 167A after starting to dry.
*Flower pollen color*.—About Light Greyed-Orange 163C when first opened.
*Position*.—Perigynous.

Pistil:
*Number*.—Usually one.
*Average length*.—Approximately 9 mm.
*Ovary diameter*.—Approximately 0.5 mm.
*Pubescence*.—None.
*Stigma extension in comparison to anthers*.—Level or slightly above anthers.
*Style frequency of supplementary pistils*.—Absent.
*Color*.—About Medium Yellow-Green 144B.

Flower-buds:
*Hardiness*.—Hardy in central San Joaquin Valley, Calif.
*Size*.—Medium.
*Length*.—Medium, approximately 1.8 mm.
*Shape*.—Pointed.
*Positioning*.—Slightly free.
*Pubescence*.—Absent.
*Color*.—About Dark Greyed-Orange 177A.

Receptacle:
*Depth*.—Medium, approximately 3 mm.
*Pubescence of inner surface*.—Absent.
*Pubescence of outer surface*.—Absent.

FRUIT

General: (Description taken near Wasco, Kern County, Calif. on Jun. 15, 2013). Date of first pick: Approximately June 11. Date of last pick: Approximately June 21.
*Maturity when described*.—Firm.
*Season ripening*.—Early. Starting about June 11 and continuing until June 21.
*Position of maximum diameter*.—Towards the middle.
*Symmetry about the suture*.—Symmetric.
*Shape of base*.—Rounded.

Size:
*Length (stem end to apex)*.—Approximately 55 mm.
*Diameter in line with suture plane*.—Approximately 55 mm.
*Diameter perpendicular to suture plane*.—Approximately 60 mm.
*Average weight*.—Approximately 128 gm.

Form:
*Viewed from apex*.—Round, symmetrical.
*Viewed from side, facing suture*.—Rounded, with high shoulders.
*Viewed from side, perpendicular to suture*.—Rounded.

Apex shape: Flattened.
Apex base: Rounded.

Fruit stem cavity:
*Shape*.—Flaring.
*Depth*.—Medium; Approximately 8 mm.
*Breadth*.—Approximately 8 mm.
*Width*.—Medium, approximately 8 mm.

Fruit stem:
*Length*.—Medium; approximately 8 mm.
*Diameter*.—Approximately 2 mm.
*Color*.—About Medium Green 143C.
*Adherence to stone*.—Medium.

Fruit skin:
*Thickness*.—Medium, approximately 0.8 mm.
*Adherence to flesh*.—Medium.
*Surface texture*.—Smooth.
*Pubescence*.—None.
*Bloom*.—Slight.
*Ground color*.—Not visible.
*Overcolor*.—About Dark Greyed-Purple 187A.
*Relative area of overcolor*.—Large.
*Pattern of overcolor*.—Solid flush only.
*Taste*.—Mild.
*Reticulation*.—Slight.
*Roughness*.—Absent.
*Tenacity*.—Tenacious to flesh.
*Tendency to crack*.—Slight.

Flesh:
*Ripens*.—Evenly.
*Texture*.—Crisp-juicy.
*Fibers*.—Medium.
*Flavor*.—Mild.

*Brix*.—Approximately 18°.
*Juice*.—Abundant to moderate.
*Aroma*.—Slight.
*Color*.—About Medium Red 46C.
*Anthocyanin color around stone*.—Strongly expressed.
*Anthocyanin color of flesh*.—Strongly expressed.
*Amygdalin*.—Wanting.
*Acidity*.—Low.
*Sugar content*.—High.
*Eating quality*.—Good.
*Stone/flesh ratio*.—About 1/30.
*Firmness*.—Medium.

Pit cavity size:
*Length*.—Approximately 18 mm.
*Diameter perpendicular to suture plane*.—Approximately 15 mm.
*Diameter in line with suture*.—Approximately 9 mm.
*Color*.—About Medium Red 46C.

Fruit use: Fresh market.

Fruit shipping and keeping quality: Good.

Stone:
*Stone freeness*.—Cling.
*Degree of adherence to flesh*.—Medium.
*Stone size*.—Size: Medium Size compared to Fruit: Small. Length: Medium, approximately 18 mm. Diameter in line with suture plan: Approximately 15 mm. Diameter perpendicular to suture plane: Approximately 9 mm. Width of Stalk End: Medium, Approximately 4 mm. Angle of Stalk end: Right angle. Hilum: Oval.
*Stone form*.—Viewed from side: Nearly ovoid. Viewed from ventral end: Flattened, symmetrical. Viewed from Stem end: Flattened, symmetrical.
*Stone shape*.—Base shape: Nearly straight. Apex shape: Rounded with small sharp point.
*Stone surface*.—Slightly smooth to irregular.
*Stone halves*.—Nearly symmetrical.
*Stone ridges*.—Rounded, continuous.
*Stone outgrowing keel*.—Well-developed.
*Stone tendency to split*.—Almost none.
*Stone color*.—About Medium Greyed-Orange 164A to Light Greyed-Orange 164C when dried.
*Position of maximum*.—Middle.
*Sides*.—Nearly equal.
*Pits*.—Shallow, not well developed.
*Fibers*.—Parts from flesh smoothly.
*Ventrical edge*.—Medium.
*Dorsal edge*.—Narrow.
*Ground color*.—Not visible.
*Overcolor*.—Very large.
*Pattern of overcolor*.—None.

Suture:
*Line*.—Shallow.

Ventral surfaces:
*Lips*.—Nearly equal.
*Depression of apex*.—Indistinct.
*Pistil base*.—Not persistent.
*Pubescence at apex*.—Absent.

Pistil point:
*Shape*.—Flattened.

What is claimed is:

1. A new and distinct plum tree as herein described and illustrated.

* * * * *

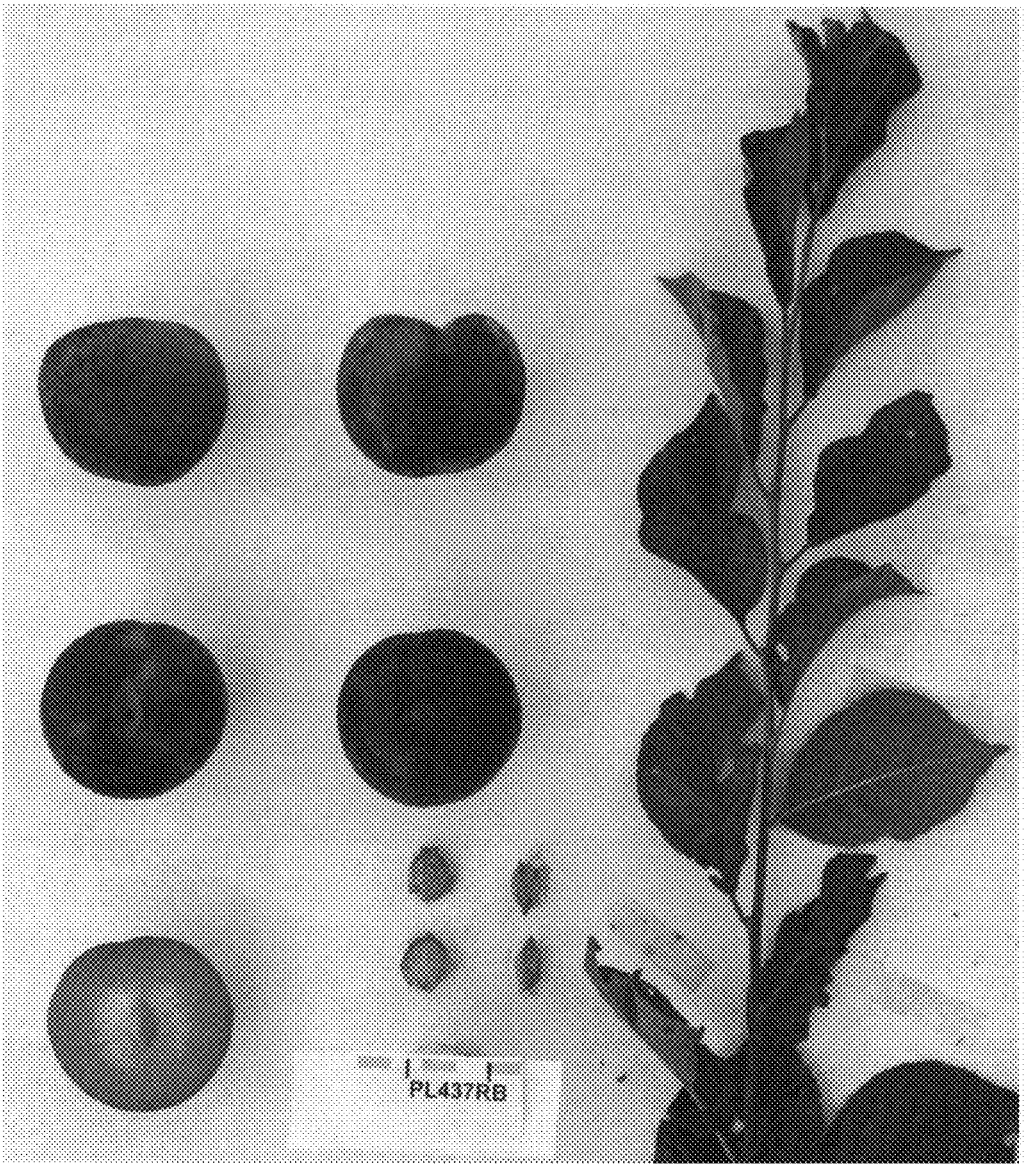
PL437RB

UNITED STATES PATENT AND TRADEMARK OFFICE

CERTIFICATE OF CORRECTION

PATENT NO. : PP26,175 P3
APPLICATION NO. : 13/998414
DATED : December 1, 2015
INVENTOR(S) : Terry A. Bacon It is certified that error appears in the above-identified patent and that said Letters Patent is hereby corrected as shown below:

IN THE SPECIFICATION

In column 3 at line 52 (approx.), Change "Moderate," to --Medium,--.

In column 4 at line 58, Change "07.mm." to --0.7 mm.--.

In column 8 at line 14 (approx.), Change "Ventrical" to --Ventricle--.

Signed and Sealed this
Seventh Day of June, 2016

Michelle K. Lee

Michelle K. Lee
*Director of the United States Patent and Trademark Office*